(12) United States Patent
Sacchetti et al.

(10) Patent No.: US 9,279,800 B2
(45) Date of Patent: *Mar. 8, 2016

(54) APPARATUS, METHOD, SYSTEM FOR THE DETERMINATION OF THE AGGREGATION RATE OF RED BLOOD CELLS

(71) Applicant: Alcor Scientific, Inc., Warwick, RI (US)

(72) Inventors: Peter Sacchetti, Attleboro, MA (US); Francesco Frappa, Udine (IT)

(73) Assignee: Alcor Scientific, Inc., Smithfield, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/176,307

(22) Filed: Feb. 10, 2014

(65) Prior Publication Data
US 2014/0154733 A1 Jun. 5, 2014

Related U.S. Application Data

(63) Continuation of application No. 13/740,843, filed on Jan. 14, 2013, now Pat. No. 8,647,886.

(60) Provisional application No. 61/586,502, filed on Jan. 13, 2012.

(51) Int. Cl.
*G01N 33/49* (2006.01)
*G01N 21/51* (2006.01)

(52) U.S. Cl.
CPC ............ *G01N 33/4915* (2013.01); *G01N 21/51* (2013.01)

(58) Field of Classification Search
IPC ........................................ G01N 33/4915,21/51
See application file for complete search history.

(56) References Cited

U.S. PATENT DOCUMENTS

| | | | |
|---|---|---|---|
| 5,506,145 | A | 4/1996 | Bull et al. |
| 5,827,746 | A | 10/1998 | Duic |
| 5,914,242 | A | 6/1999 | Honkanen et al. |
| 6,336,358 | B1 | 1/2002 | Kishimori et al. |

(Continued)

FOREIGN PATENT DOCUMENTS

| | | |
|---|---|---|
| DE | 3338364 A1 | 5/1984 |
| EP | 0414223 | 2/1991 |

(Continued)

OTHER PUBLICATIONS

Shin et al., "Light-transmission aggregometer using a vibration-induced disaggregation mechanism," Review of Scientific Instruments 76:016107-1-016107-4, 2005.*

(Continued)

*Primary Examiner* — Rosanne Kosson
(74) *Attorney, Agent, or Firm* — Adler Pollock & Sheehan P.C.; Daniel J. Holmander, Esq.; George N. Chaclas, Esq.

(57) ABSTRACT

The present invention generally relates to an apparatus, method, system for the determination of the aggregation rate of red blood cells. More specifically, the invention concerns a method, system, and the relative apparatus used to determine the aggregation rate of red blood cells, and other parameters related to these, such as viscosity, deformability, elasticity, density, in the field of in vitro medical analyses, using optical systems after or during inducted forces for red blood cell disruption and redistribution generated by ultrasound waves.

20 Claims, 1 Drawing Sheet

(56) References Cited

U.S. PATENT DOCUMENTS

| | | |
|---|---|---|
| 6,342,391 B1 | 1/2002 | Chen et al. |
| 6,514,766 B2 | 2/2003 | Spillert et al. |
| 6,531,321 B1 | 3/2003 | Ryan et al. |
| 6,632,679 B1 | 10/2003 | Breda |
| 6,711,424 B1 | 3/2004 | Fine et al. |
| 6,974,701 B2 | 12/2005 | Bouboulis |
| 7,043,289 B2 | 5/2006 | Fine et al. |
| 7,207,939 B2 | 4/2007 | Husher |
| 7,317,939 B2 | 1/2008 | Fine et al. |
| 7,541,191 B2 | 6/2009 | Duic |
| 7,833,489 B2 | 11/2010 | Chen |
| 8,647,886 B1 * | 2/2014 | Sacchetti et al. .............. 436/165 |

FOREIGN PATENT DOCUMENTS

| | | |
|---|---|---|
| EP | 0529420 A2 | 3/1993 |
| KR | 20050014040 | 2/2005 |
| WO | WO 2008072870 | 6/2008 |
| WO | 2009050757 A2 | 4/2009 |

OTHER PUBLICATIONS

Mullaney et al., "Cell sizing: a light scattering photometer for rapid volume determination," Rev Sci Instruments 40 (8):1029-1032, 1969.

Chen, S. et al., "Monitoring of red blood cell aggregatibility in a flow-chamber by computerized image analysis", Clin Hemorheol Microcirc, 14: 497-508, 1994.

Supplementary European Search Report, pp. 1-10, Dec. 4, 2015.

Alexander V. Priezzhev et al., Aggregation and Disaggregation of Erthyocytes in Whole Blood, study by Backscattering Technique, Journal of Biomedical Optics, vol. 4, No. 1.

* cited by examiner

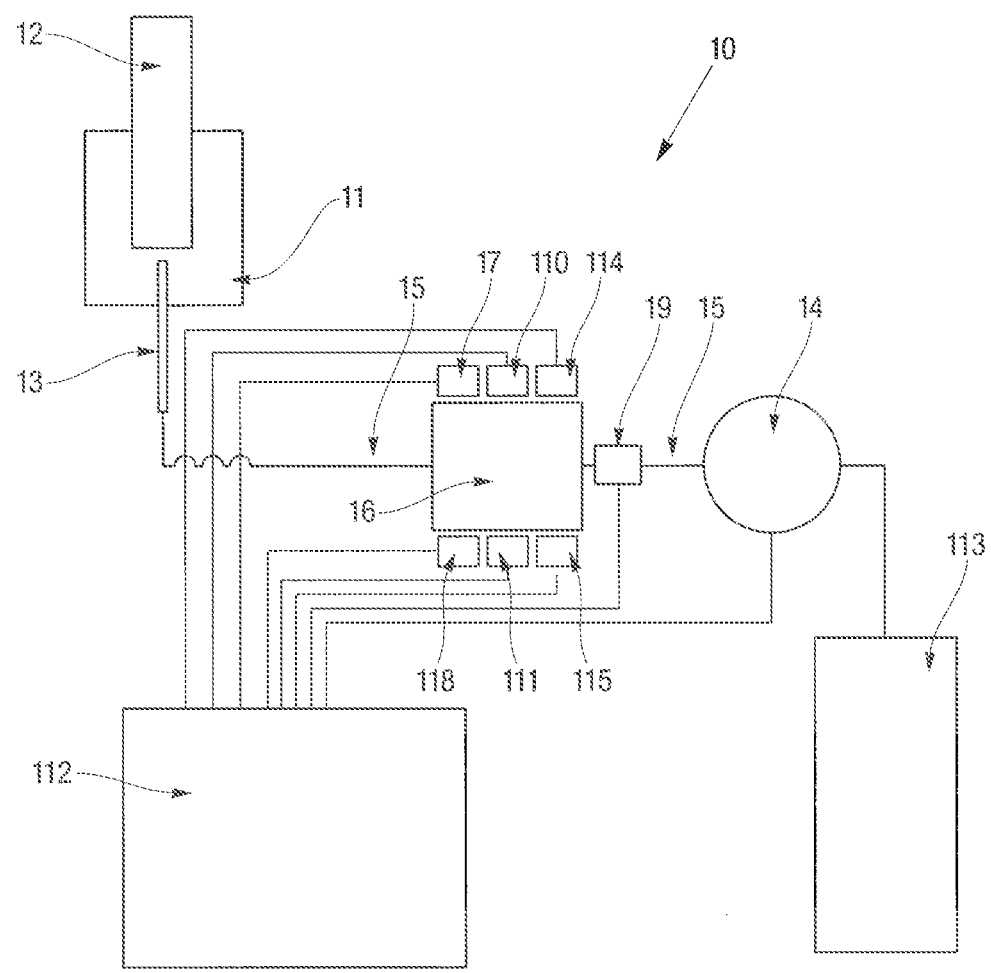

APPARATUS, METHOD, SYSTEM FOR THE DETERMINATION OF THE AGGREGATION RATE OF RED BLOOD CELLS

CROSS REFERENCE TO RELATED APPLICATION

This application is related to and claims priority from earlier filed U.S. Non-Prov. patent application Ser. No. 13/740,843 filed Jan. 14, 2013, which issued as U.S. Pat. No. 8,647,886 on Feb. 11, 2014, and U.S. Provisional Application for Patent Ser. No. 61/586,502 filed Jan. 13, 2012, the entire contents of both are incorporated herein by reference.

BACKGROUND OF THE INVENTION

The present invention generally relates to an apparatus, method, system for the determination of the aggregation rate of red blood cells. More specifically, the invention concerns a method, system, and the relative apparatus used to determine the aggregation rate of red blood cells, and other parameters related to these, such as viscosity, deformability, elasticity, density, in the field of in vitro medical analyses, using optical systems after or during inducted forces for red blood cell disruption and redistribution generated by ultrasound waves.

The state of the art for the determination of a test value corresponding to blood subsidence from a aggregogram or syllectogram of a blood sample is ascertained by reference to the article "Syllectometry, a new method for studying rouleaux formation of red blood cells" by Zijlstra published in 1963.

Aggregation is the first of three phases describing the sedimentation rate that is composed by: 1) Aggregation 2) Precipitation and 3) Packing. Erythrocyte Sedimentation Rate, which Westergren method is considered the gold standard method, is extensively used as a screening test for the determination of inflammatory status of a patient.

In the sedimentation phenomenon, aggregation is the first and the fastest among the three phases, which lasts less than two minutes, where red blood cells (RBC) forming chains (face to face aggregates) termed "Ruloux". This phase is reversible by mixing action, due, for example, with the repeated inversion of the test tube containing the sample. Rulouxformation causes are still not completely clear; the most important causes are related to proteins dispersed in plasma, such as fibrinogen. However, it is known that aggregation between RBC is strictly related to infections, inflammatory and connective tissue disorders.

A second stage aggregation phase, after Ruloux formation, spherical aggregates are formed between Ruloux with uniform increased mass, that sediment, after an initial acceleration, at constant speed conforming Stokes law. This second phase is called precipitation, and is the phase evaluated during the Westergren (WG) standard method.

As Stokes law describes that the constant speed is a balance between gravity force, viscosity and hydrostatic stress. The viscosity in a fluid as plasma is heavy affected by thermal effects and can modify sedimentation rate independently the encountered Ruloux level. Also lipids dispersed in plasma, in conjunction with lipoproteins, can increase viscosity and reduce the precipitation phase and the resulting sedimentation rate measure.

Syllectometry is a measuring method that is commonly used to determine the red blood cell aggregability, which can be related to consequent sedimentation rate. As reference, in syllectometry light is incident to a layer where the sample is exposed to shear stress. Luminous flux attenuation/increase or backscatter ultrasound wave are used for determination of variations in sample density after the abrupt stop of driving mechanism. The subsequent time-dependent plot is called syllectogram.

Therefore, there remains a need in the prior art for an apparatus, method, system for the determination of the aggregation rate of red blood cells which does not require a stopped flow technique for aggregation kinetic detection.

BRIEF SUMMARY OF THE INVENTION

The invention preserves the advantages of prior apparatus, methods, and systems for the determination of the aggregation rate of red blood cells. In addition, it provides new advantages not found in currently available apparatus, methods, and systems for the determination of the aggregation rate of red blood cells and overcomes many disadvantages of such currently available systems.

The present invention generally relates to an apparatus, method, system for the determination of the aggregation rate of red blood cells. More specifically, the invention concerns a method, system, and the relative apparatus used to determine the aggregation rate of red blood cells, and other parameters related to these, such as viscosity, deformability, elasticity, density, in the field of in vitro medical analyses, using optical systems after or during inducted forces for red blood cell disruption and redistribution generated by ultrasound waves.

The invention provides a method and the relative reusable apparatus for the determination of aggregation rate index, and subsequent erythrocytes sedimentation rate for whole blood samples. The invention reduces the complexity of the pumping systems removing the need of the stopped flow condition. The invention provides other rheological parameters such as viscosity, deformability, elasticity, density. The invention provides a method and the relative apparatus for reduce the sample mixing time needed for the disruption of the aggregates RBC chains, using an alternative method prior and during the rheological behavior detection. The invention reduces the amount of sample volume needed for avoid contamination by residuals of previous sample applying an enhanced washing system.

BRIEF DESCRIPTION OF THE DRAWINGS

The novel features which are characteristic of the present invention are set forth in the appended claims. However, the invention's preferred embodiments, together with further objects and attendant advantages, will be best understood by reference to the following detailed description taken in connection with the accompanying drawing in which:

FIG. 1 is a schematic view of an embodiment of the apparatus, method, and system for the determination of the aggregation rate of red blood cells.

DETAILED DESCRIPTION OF THE PREFERRED EMBODIMENTS

In accordance with the invention of FIG. 1, the present invention 10 generally relates to an apparatus, method, system for the determination of the aggregation rate of red blood cells. More specifically, the invention 10 concerns a method, system, and the relative apparatus used to determine the aggregation rate of red blood cells, and other parameters related to these, such as viscosity, deformability, elasticity, density, in the field of in vitro medical analyses, using optical systems after or during inducted forces for red blood cell disruption and redistribution generated by ultrasound waves.

The invention provides a method and the relative reusable apparatus for the determination of aggregation rate index, and subsequent erythrocytes sedimentation rate for whole blood samples. The invention reduces the complexity of the pumping systems removing the need of the stopped flow condition. The invention provides other rheological parameters such as viscosity, deformability, elasticity, density. The invention provides a method and the relative apparatus for reduce the sample mixing time needed for the disruption of the aggregates RBC chains, using an alternative method prior and during the rheological behavior detection. The invention reduces the amount of sample volume needed for avoid contamination by residuals of previous sample applying an enhanced washing system.

In one embodiment, the apparatus 10 for the determination of RBC aggregation, and their subsequent sedimentation rate, according to the invention comprises a reading cell container 16 where the sample is introduced. The apparatus 10 provides this reading cell container 16 equipped with two parallel optical windows for allow to a light radiation to pass through the sample herein introduced or reading the backscatter of the incident light. The apparatus 10 comprises a collimated light source composed in such way that light passes through the windows of the container mentioned above, and can be reflected. On the opposite side of the light source 17 is present an optical detector 18 for the evaluation of the light attenuated by the sample. The optical detector 18 could be positioned on the same side of the light source 17 for the detection of the light scattering. The reading cell container 16 is equipped with electromechanical actuator 110,111 able to vibrate the sample herein introduced, disrupting the aggregates naturally present in the blood sample, and evenly distribute the erythrocytes within the entire volume of sample. The apparatus has a temperature control system 114, 115 for the sample container for standardize the reaction environment.

The apparatus 10 comprises further an electronic control device 112 able to acquire the optical variance detected by the optical detector, drive the electromechanical actuators 110, 111 and acquire the container temperature values. This electronic control device 112 is also able to convert the detected time dependent light variation into an aggregation index and his subsequent erythrocyte sedimentation rate, providing the result of the evaluated phenomenon in the way of numerical result comparable to the common used parameters used in a clinical laboratory.

According with another embodiment of the invention, an apparatus 10 or system has been developed. The apparatus or system 10 is comprised of a mixer device 11 for a low homogenization of the sample inside a collection tube 12. The homogenization can be achieved by a Vortex like mixer or by the radial or axial rotation of the sample tube.

After the homogenization the sample is then withdrawn by a needle 13 and aspirate by a pump device 14 through hydraulic circuit 15. The hydraulic circuit 15 connects the aspiration needle 13 to the reading cell container 16 allow their filling by the sample, guaranteed by the optical sensor composed by the emitter 17 and an optical receiver 18 and a secondary optical flow sensor 19 controlled by an electronic control device 112.

The light emitter source 17 is composed, in one embodiment but not in limitative manner, by a Light Emitter Diode (LED), and can be substituted, for example, by a laser source or an incandescent lamp. The optical receiver 18, in this embodiment but not in limitative manner, is composed by CCD sensor for two dimensional characterization of the reaction. This sensor can be substitute by a single receiver element such as photodiode, photomultiplier etc.

After the complete or desired filling of the reading cell 16 the pump device 14 is stopped by the electronic control device 112, and the sample is processed by the electromechanical devices 110, 111, for example composed by piezoceramics, activated to a predetermined power by the control device 112, to disrupt aggregates and evenly re-suspend the RBC on the sample volume. A prerequisite for an aggregation kinetic detection is a complete disruption of the aggregates, normally formed in a steady state of the sample. This disruption can be achieved by an intensive mixing phase before and during the transportation of the sample in the reading cell or detection.

As an alternative to a predetermined power, the piezoceramic power is initially ramped up to a level where cell emulsification is detected through the optical reading. This process is stopped and a duplicate sample is introduced. The power applied can be optimized at fraction of the emulsification power level which results in maximum dispersion, without cell damage.

During this phase the control device 112 acquires the signal detected by the optical receiver 18 and stops the electromechanical devices 110, 111 or actuators when the light variation detected by the receiver 18 stops decreasing, indicating the complete disruption of the aggregate present into the sample. This recorded plot expresses the disruption rate of the RBC and is post evaluated by the system.

In one embodiment, the shape of the reading cell container 16 walls comprises sound lenses for focusing the wave pressure shear to emphasize the shear inducted to the sample.

After the electromechanical devices 110,111 stops, the signal detected by the receiver 18 is still recorded by the control device 112 for a predetermined amount of time as a plot of kinetic aggregation.

After the end of the acquisition the sample is evacuated from the reading cell 16 by the pump device 14 to a waste reservoir 113. During the evacuation, the electromechanical devices 110, 111 are activated with a high power for remove proteins eventually bonded to the reading cell container 16 walls. An evacuation of the reading chamber avoids the pollution of the sample currently under measure by the residual of the previous measured sample with washing and does not require a large flow amount of sample currently under measure for removal the residuals of the previous measured sample. After the evacuation, the system is ready for a new sample withdrawing and analysis.

The reading cell container 16 is also maintained to a controlled temperature by the thermoelectric device 114 and the temperature is acquired by the control device 112 through the temperature sensor 115 for providing standardized conditions of reaction.

During the dispersion phase induced by the electromechanical devices 110, 111, the resultant signal is evaluate to extract the mean viscosity value of the sample plasma by considering the time need by the sample to completely re-suspend. After a complete re-suspension of the sample a burst of ultrasound waves is inducted to the sample for evaluating the red blood cell deformability. This deformability is considered as the time needed by the media to absorb the wave shear impressed, also decay after the wave share absorption is evaluated in function of time as index of the mean shape recovery ability.

It should be appreciated that the system, method, and apparatus may include one or more components or steps listed above in a variety of configurations depending upon desired performance or requirements.

It would be appreciated by those skilled in the art that various changes and modifications can be made to the illustrated embodiments without departing from the spirit of the present invention. All such modifications and changes are intended to be within the scope of the present invention.

What is claimed is:

1. An apparatus for determining the aggregation rate of red blood cells, comprising:
   a) a hydraulic circuit having a pump for transporting a blood sample portion comprising red blood cells that have aggregated;
   b) a reading cell container operationally connected to the hydraulic circuit configured for receipt of the blood sample portion;
   c) a light emitter source positioned about the reading cell to pass light through the blood sample portion;
   d) an optical receiver positioned opposite the light emitter source and about the reading cell to detect light passing through the blood sample portion;
   e) a disruption mechanism connected to the reading cell container for disruption of the red blood cell aggregates within the blood sample portion to assist in recording a disruption rate; and
   f) a main controller operationally connected to the disruption mechanism, the main controller configured to activate the disruption mechanism for the disruption of the red blood cell aggregates within the blood sample portion until light detected stops decreasing, indicating the disruption of aggregates within the blood sample portion,
   whereby, in a method of using the apparatus, after the disruption mechanism is stopped, the main controller records an aggregation rate of the red blood cells of the blood sample portion for a predetermined time based upon detected light variation.

2. The apparatus of claim 1, further comprising:
   a fluid reservoir connected to the reading cell container for receipt of an evacuated blood sample portion from the reading cell container.

3. The apparatus of claim 1, wherein the apparatus comprises an evacuation mechanism to evacuate the evacuated blood sample portion from the reading cell container.

4. The apparatus of claim 3, wherein the evacuation mechanism is configured to provide ultrasound stress to the reading cell container.

5. The apparatus of claim 1, wherein the apparatus determines an aggregation index of the red blood cells for a subsequent estimation of an erythrocyte sedimentation rate, the determination steps being comparable to those in a Westergren method.

6. The apparatus of claim 1, wherein the apparatus determines a disruption index of the red blood cells as rheological parameters usable for pathologic detection purposes.

7. The apparatus of claim 1, wherein the apparatus determines a mean red blood cells shape recovery ability.

8. The apparatus of claim 1, wherein the apparatus determines the plasma viscosity.

9. The apparatus of claim 1, wherein the reading cell container is configured for the optical detection of aggregation reaction.

10. The apparatus of claim 1, wherein the disruption mechanism is an actuator.

11. The apparatus of claim 1, wherein the disruption mechanism is an ultrasonic inducted mechanism for the disruption of red blood cells aggregates.

12. The apparatus of claim 1, wherein the disruption mechanism is electric power applied to a piezoceramic material which is initially ramped up to a level where cell emulsification is detected through the optical reading cell.

13. A method of measuring the disruption rate and the aggregation rate of a sample of red blood cells, comprising:
   a) obtaining a blood sample portion comprising aggregated red blood cells;
   b) providing the apparatus of claim 1;
   c) delivering the blood sample portion into the reading cell container;
   d) disrupting the aggregates in the blood sample portion within the reading cell container to distribute and resuspend the red blood cells;
   e) passing light through the blood sample portion within the reading cell container;
   f) receiving and detecting light emitted from the reading cell container;
   g) recording a disruption rate of the red blood cell aggregates within the blood sample portion based upon the light variation;
   h) continuing the disruption of the blood sample portion within the reading cell until the variation in light detected stops decreasing, indicating the disruption of the red blood cell aggregates within the blood sample portion;
   i) recording an aggregation rate of the red blood cells in the blood sample portion for a predetermined time based upon detected light variation; and
   j) evacuating the blood sample portion from the reading cell container.

14. The apparatus of claim 1, wherein the apparatus determines an aggregation index of the red blood cells for subsequent estimation of an erythrocyte sedimentation rate.

15. The method of claim 14, wherein disrupting the blood sample portion comprises applying electric power to a piezoceramic material initially ramped up to a level where cell emulsification is detected through the optical reading.

16. An apparatus for determining the aggregation rate of red blood cells, comprising:
   a) a hydraulic circuit for transporting a blood sample portion comprising aggregated red blood cells;
   b) a reading cell container configured to receive the blood sample portion from the hydraulic circuit;
   c) a light emitter source to pass light through the blood sample portion while the blood sample portion is in the reading cell container;
   d) an optical receiver positioned to detect light passing from the light emitter source through the blood sample portion while the blood sample portion is in the reading cell container;
   e) a disruption mechanism connected to the reading cell container to disrupt the aggregated red blood cells within the blood sample portion while the blood sample portion is in the reading cell container; and
   f) a main controller configured to selectively activate the disruption mechanism and record an aggregation rate of the red blood cells in the blood sample portion based upon detected light variation.

17. The apparatus of claim 16, further comprising:
   g) a fluid reservoir connected to the reading cell container for receipt of a blood sample portion evacuated from the reading cell container; and
   h) an evacuation mechanism to evacuate the blood sample portion from the reading cell container, wherein the evacuation mechanism is configured to provide ultrasound stress to the reading cell container.

18. The apparatus of claim 16, wherein the main controller determines the aggregation rate based upon for a predetermined time of disruption.

19. The apparatus of claim 16, wherein the main controller determines the aggregation rate based upon data collected from a start of disruption until light detected stops decreasing.

20. An apparatus for determining the aggregation rate of red blood cells, comprising:
- a) a reading cell container configured to receive a blood sample portion comprising aggregated red blood cells from a hydraulic circuit;
- b) a light emitter source to pass light through the blood sample portion while the blood sample portion is in the reading cell container;
- c) an optical receiver positioned to detect light passing from the light emitter source through the blood sample portion while the blood sample portion is in the reading cell container;
- d) a disruption mechanism connected to the reading cell container to disrupt the aggregated red blood cells within the blood sample portion while the blood sample portion is in the reading cell container; and
- e) a main controller configured to record an aggregation rate of the red blood cells in the blood sample portion based upon detected light variation.

* * * * *